United States Patent
Maki et al.

(10) Patent No.: US 6,237,256 B1
(45) Date of Patent: May 29, 2001

(54) BALANCE-ENHANCED INSERT FOR FOOTWEAR

(75) Inventors: Brian E. Maki, Don Mills; Stephen D. Perry, Toronto; William E. McIlroy, Guelph, all of (CA)

(73) Assignee: Sunnybrook and Women's College Health Sciences Centre, Toronto (CA)

( * ) Notice: Subject to any disclaimer, the term of this patent is extended or adjusted under 35 U.S.C. 154(b) by 0 days.

(21) Appl. No.: 09/494,657

(22) Filed: Jan. 31, 2000

Related U.S. Application Data (63) Continuation-in-part of application No. 09/132,429, filed on Aug. 12, 1998, now abandoned.

(51) Int. Cl.[7] .......................... A43B 13/18; A43B 23/00; A43B 7/14; A61F 5/14

(52) U.S. Cl. ................................... 36/140; 36/88; 36/28; 36/43; 36/141; 36/176

(58) Field of Search .................................. 36/88, 92, 91, 36/25 R, 28, 30 R, 43, 44, 140, 141, 142, 143, 144, 173, 174, 176, 178, 180, 181

(56) References Cited

U.S. PATENT DOCUMENTS

| D. 281,735 | 12/1985 | Seltzer . |
|---|---|---|
| D. 305,954 | 2/1990 | Kin . |
| D. 350,848 | 9/1994 | Tzenos . |
| D. 373,013 | 8/1996 | Rosetta . |
| 1,194,152 | 8/1916 | Douglas . |
| 1,929,126 | 10/1933 | Tuki et al. . |
| 1,952,687 | 3/1934 | Sawmiller . |
| 2,114,700 | 4/1938 | Bradbury . |
| 2,284,930 | 6/1942 | Stoker . |
| 3,757,774 | 9/1973 | Hatuno . |
| 4,020,570 | 5/1977 | Shames . |
| 4,033,054 | 7/1977 | Fukuoka . |
| 4,047,310 | 9/1977 | Sunoo . |

(List continued on next page.)

OTHER PUBLICATIONS

Black et al., "Aging, Imbalance, and Falls", In: Barber H., Sharpe J. (Eds.), Vestibulo–ocular Reflex, Nystagmus and Vertigo. Raven Press, New York, 1993, pp. 317–335.

Maki et al., "Accidents: falls", In: Birren J.E. (Ed.), Encyclopedia of Gerontology: Age, Aging and the Aged. Academic Press, San Diego, 1996, vol. 1, pp. 11–18.

Maki, "Gait changes in older adults: predictors of falls or indicators of fear?", Journal of the American Geriatrics Society 1997; 45:313–320.

Maki et al., "Postural control in the older adult" In: Studenski, S. (Ed.), Clinics in Geriatric Medicine: Gait and Balance Disorders. W.B. Saunders, Philadelphia, 1996; 12(4): 635–658.

Maki et al., "The role of limb movements in maintaining upright stance: the 'change in support' strategy", Physical Therapy 1997; 77:488–507.

(List continued on next page.)

*Primary Examiner*—Paul T. Sewell
*Assistant Examiner*—Anthony Stashick
(74) *Attorney, Agent, or Firm*—Ridout & Maybee LLP (57) ABSTRACT

An article of footwear and insert for an article of footwear are provided with means for stimulating cutaneous pressure sensation from the perimeter of the plantar surface (sole) of the foot. Increasing cutaneous sensation from the perimeter of the plantar foot surface provides the central nervous system of the wearer of the footwear with an increased ability to detect and react to shifts of the body's center of gravity toward the edges of the feet which, if left uncorrected, could result in a loss of balance or a fall. An insole is disclosed which is provided with an elongate member or a series of protrusions which form a narrow ridge in close proximity to the perimeter of the insole, the ridge being adapted to protrude upwardly against the plantar foot surface along at least a portion of the perimeter thereof.

14 Claims, 12 Drawing Sheets

U.S. PATENT DOCUMENTS

| | | |
|---|---|---|
| 4,109,661 | 8/1978 | Fukuoka . |
| 4,215,492 | 8/1980 | Sandmeier . |
| 4,345,387 | 8/1982 | Daswick . |
| 4,674,203 | 6/1987 | Goller . |
| 4,694,831 | 9/1987 | Seltzer . |
| 4,760,655 | 8/1988 | Mauch . |
| 4,897,937 | 2/1990 | Misevich et al. . |
| 4,955,148 | 9/1990 | Padilla . |
| 5,005,300 | 4/1991 | Diaz et al. . |
| 5,005,575 | 4/1991 | Geri . |
| 5,063,692 | 11/1991 | Suginaka . |
| 5,146,698 | 9/1992 | Tilles et al. . |
| 5,400,526 | 3/1995 | Sessa . |
| 5,469,638 | 11/1995 | Crawford, III . |
| 5,551,173 | 9/1996 | Chambers . |
| 5,564,989 | 10/1996 | Larsen . |
| 5,647,145 | 7/1997 | Russell et al. . |
| 5,664,342 | 9/1997 | Buchsenschuss . |
| 5,682,690 | 11/1997 | Chang . |
| 5,685,094 | 11/1997 | Lin . |
| 5,694,705 | 12/1997 | Alonso Coves . |
| 5,704,137 | 1/1998 | Dean et al. . |

OTHER PUBLICATIONS

Maki, "Prediction and prevention of falls in the elderly", $9^{th}$ Biennial Conference of the Canadian Society for Biomechanics, Burnaby, British Columbia, Aug. 1996.

Maki, "Prediction and prevention of falls in the elderly", Dizziness Update '96, Toronto, Oct., 1996.

Asai et al., "The influence of foot soles cooling on standing postural control", In: Brandt T. et al. (Eds.) Disorders of Posture and Gait. New York: George Thieme–Verlag, 1990, 198–201.

Asai et al., "The influence of foot soles . . . ", In: Woollacott M. et al. (Eds.) Posture and Gait: Control Mechanisms, vol. II. Eugene OR: University of Oregon Books, 1992, 151–154.

Asai et al., "Limiting factor for movable range of the centre of foot pressure . . . ", In: Taguchi et al. (Eds.) Vestibular and Neural Front. Tokyo: Elsevier, 1994, 525–528.

Okubo et al., "Study on influences of the plantar mechanoreceptor on body sways", Agressologie 1980; 21:61–69.

Watanabe et al., "The role of the plantar mechanoreceptor in equilibrium control", Annals of the New York Academy Sciences 1981; 374:855–864.

Magnusson et al., "Significance of Pressor Input from the Human Feet in Lateral Postural Control", Acta Otolaryngol 1990; 110:321–327.

Magnusson et al., "Significance of Pressor Input from the Human Feet in Anterior–Posterior Postural Control", Acta Ololaryngol 1990; 110:182–188.

Wu et al., "The significance of somatosensory stimulations to the human foot in the control of postural reflexes", Exp. Brain Res. (1997) 114:163–169.

BALANCE-ENHANCED INSERT FOR FOOTWEAR

CROSS-REFERENCES TO RELATED APPLICATIONS

This application is a continuation-in-part of U.S. patent application Ser. No. 09/132,429, filed on Aug. 12, 1998, now abandoned.

STATEMENT REGARDING FEDERALLY SPONSORED RESEARCH OR DEVELOPMENT

The invention was made with government support under Grant No. 1 R01 AG12165-01A2 awarded by National Institutes of Health National Institute on Aging. The government has certain rights in the invention.

FIELD OF THE INVENTION

The present invention relates to inserts for footwear, as well as footwear incorporating such inserts, which stimulate cutaneous pressure sensation from the edges of the feet (perimeter of the plantar foot surface) during standing and walking, and thereby improve the ability of the wearer's central nervous system to keep the body's center of gravity balanced and centered over the feet, particularly in persons who experience postural instability as a result of loss of cutaneous touch and pressure sensation due to aging or other factors.

DESCRIPTION OF THE PRIOR ART

One of the more pervasive effects of aging is a loss of cutaneous touch and pressure sensation. The loss of cutaneous sensation in the plantar surface (sole) of the feet has been correlated with impaired postural control (poor balance) and an increased risk of falling. In order to maintain stable upright stance, the center of gravity of the body must be positioned over the base of support established by the feet. Loss of balance and falling occur if the body weight is shifted too close to the limits of this base of support, i.e. too close to the perimeter of the plantar foot surface.

Numerous experimental studies support the important contribution of cutaneous sensation, from the plantar foot surface, in the control of postural balance. This cutaneous sensation acts, within the central nervous system, to trigger and/or modulate the automatic postural reflexes and reactions that act to prevent loss of balance and falling.

It is known that cutaneous sensation from the plantar surface of the foot can be stimulated mechanically by standing on raised protrusions and that such stimulation can reduce the postural sway that occurs during quiet standing. For example, having a person stand on a grid of small indentors (ball bearings) contacting the entire soles of the feet was found, in a laboratory experiment, to lead to increased activation of sensory nerves and concomitant reduction in postural sway when a person is standing still. However, providing increased cutaneous stimulation within the central regions of the plantar foot surface does not provide the central nervous system with information about the proximity of the center of gravity to the perimeter of the base of support, and has not been shown to improve a person's ability to react to a loss of balance and thereby avoid a fall.

Various footwear inserts and articles of footwear have been developed which incorporate raised protrusions of various shapes and sizes in various areas of the upper and/or lower surface of the insole. Invariably, these inserts have been designed for purposes other than improving postural balance and preventing falls.

For example, Daswick (U.S. Pat. No. 4,345,387) and Rosetta (U.S. Des. Pat. No. D373,013) both disclose an inner sole which includes a plurality of upwardly extending protrusions which are located throughout various portions of the inner sole and are designed to provide cushioning. Chang (U.S. Pat. No. 5,682,690) and Selzer (U.S. Des. Pat. No. D281,735) both disclose articles of footwear having a sole with upwardly extending protrusions which are located throughout large areas of the inner sole and are intended to massage the wearer's foot during walking. Hatuno (U.S. Pat. No. 3,757,774) discloses a massage sandal having a plurality of projections extending across the entire surface of the sole for the purposes of promoting blood circulation and strengthening the connective tissues of the foot by massaging the sole of the foot during walking. Padilla (U.S. Pat. No. 4,955,148) discloses a foot support assembly which includes several broad areas of raised support for the purposes of better distributing the forces acting on the foot so as to alleviate pain or discomfort. Douglas (U.S. Pat. No. 1,194,152) discloses a cushion insole with protrusions on the undersurface designed to afford ventilation of the foot. Tuki (U.S. Pat. No. 1,929,126) discloses a resilient sole element for footwear in which protrusions on the undersurface of the insole are intended to provide comfort, to protect against ingress of moisture and to provide protection against electrical shock. Misevich at al (U.S. Pat. No. 4,897,937) disclose an insole base member which uses protrusions of various sizes and shapes to form a mechanical interlock between the insole base and the insole.

Therefore, the prior art does not contain any examples of footwear inserts or articles of footwear which improve a person's ability to react to a loss of balance and thereby avoid a fall.

SUMMARY OF THE INVENTION

The present invention overcomes disadvantages of the prior art by providing an article of footwear and an insert for an article of footwear with a means for stimulating cutaneous pressure sensation from the perimeter of the plantar foot surface (foot sole) whenever the wearer's center of gravity shifts toward the edges of the feet. The inventors have found that increasing cutaneous sensation from the perimeter of the plantar foot surface provides the central nervous system with an enhanced ability to detect, and react to, weight shifts toward the edges of the feet which, if left uncorrected, could result in a loss of balance or a fall. The inventors have found that the inserts and footwear according to the present invention are particularly effective at improving the efficacy of the balance reflexes and reactions that act to correct for the weight shifts that occur as a result of unexpected perturbation (disturbance) of balance.

Although the scope of the present invention is not to be limited by theory, it is believed that promoting cutaneous pressure sensation specifically from the perimeter of the plantar foot surfaces (foot sole) may play an important role, within the central nervous system, in determining the proximity of the body's center of gravity to the stability boundaries of the base of support established by the feet, i.e. the perimeter of the plantar foot surfaces. Center-of-gravity location, relative to the base of support, is believed to be a critical variable that is controlled by the central nervous system in maintaining upright stance.

Accordingly, in one aspect, the present invention provides a foot-contacting insert adapted to be received on an upper surface of a sole in an article of footwear, the insert stimulating cutaneous pressure sensation from the perimeter of the plantar surface of the foot whenever the wearer's center of gravity shifts toward a periphery of the plantar foot surface during standing or walking. One or more narrow, ridge-forming members is located in close proximity to the perimeter of the insert, the inner portion of the insert being smoothly contoured. During standing or walking, the ridge-forming member forms a narrow, elongate, raised ridge which protrudes upwardly against the perimeter of the plantar surface of the foot, the raised ridge being sufficiently narrow, deep and hard to cause localized indentation of the skin and associated stimulation of cutaneous pressure sensation whenever body weight is shifted toward the perimeter of the plantar foot surface.

In another aspect, the present invention provides an article of footwear including a sole having an upper foot-contacting layer adapted to stimulate cutaneous pressure sensation from the perimeter of the plantar surface of the foot whenever the wearer's center of gravity shifts toward a periphery of the plantar foot surface during standing or walking. One or more narrow, ridge-forming members is located near the perimeter of the sole, the inner portion of the sole being smoothly contoured. During standing or walking, the ridge-forming member forms a narrow, elongate, raised ridge which protrudes upwardly against the perimeter of the plantar surface of the foot, the raised ridge being sufficiently narrow, deep and hard to cause localized indentation of the skin and associated stimulation of cutaneous pressure sensation whenever body weight is shifted toward the perimeter of the plantar foot surface.

BRIEF DESCRIPTION OF THE DRAWINGS

The invention will now be described, by way of example only, with reference to the following drawings in which.

DETAILED DESCRIPTION OF THE DRAWINGS

Figure 1:
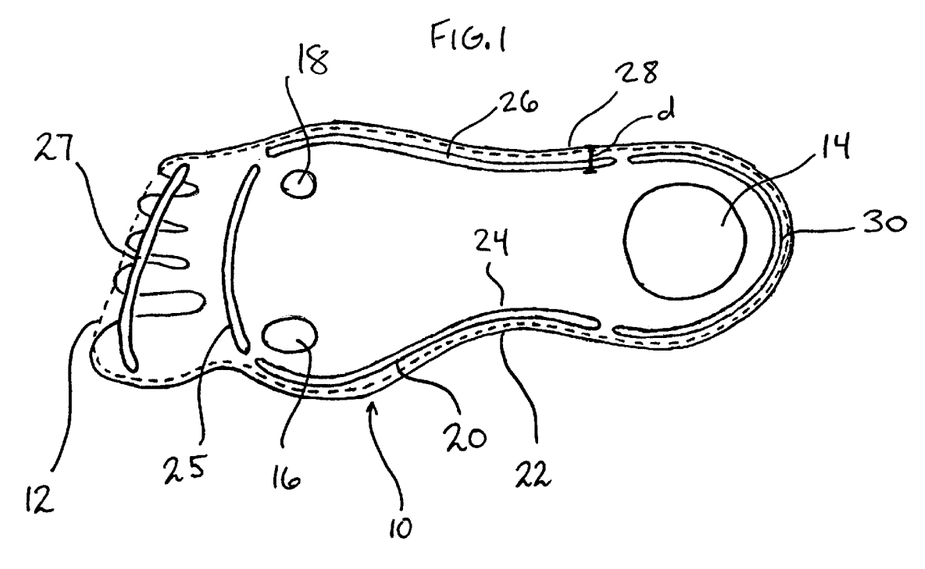
FIG. 1 illustrates an outline of a human foot showing the plantar foot surface and preferred areas for stimulation of cutaneous pressure sensation.

FIG. 1 is an outline of a human foot 10 in which a dotted line represents the outer perimeter of the area of the foot referred to herein as the plantar foot surface 12. The term "plantar foot surface" as used herein means the sole of the human foot. The plantar foot surface includes within its boundaries the calcaneus (heel) bone, schematically shown as 14, the five metatarsal bones, of which the heads (anterior extremities) of the first and fifth metatarsal bones are indicated schematically in FIG. 1 as 16 and 18, respectively, and the toes.

FIG. 1 also illustrates the narrow areas located near the perimeter of plantar foot surface 12 in which cutaneous sensation is to be stimulated in accordance with the present invention. The areas illustrated are: area 20 extending along the medial (inner) edge 22 of foot 10 from the head of the first metatarsal bone 16 to the anterior extremity of the calcaneus bone 14; area 26 extending along the lateral (outer) edge 28 of foot 10 from the head of the fifth metatarsal bone 18 to the anterior extremity of the calcaneus bone 14; and area 30 extending around the posterior edge of calcaneus bone 14. Area 20 may or may not include the instep 24 of foot 10. It is to be understood that stimulation of cutaneous sensation according to the present invention is carried out in all three areas 20, 26 and 30, or portions thereof. As further shown in FIG. 1, stimulation may also be carried out in one of two areas, or portions thereof, located near the anterior perimeter of the plantar foot surface: area 25, which extends transversely across the width of the foot, rearwardly of the toes and forward of the heads of the metatarsal bones; or area 27, which extends transversely across the foot under one or more toes.

Areas 20, 26, 27 and 30 in which cutaneous sensation is to be stimulated are to be located in close proximity to the perimeter of the plantar foot surface 12, such that the distance between each area of stimulation and the adjacent portion of the plantar foot surface perimeter 12 does not exceed a predetermined limit. As shown schematically in FIG. 1, the entire area of stimulation in areas 20, 26, 27 and 30 is within a distance d from the perimeter of the plantar foot surface 12. Distance d is not more than about 15 mm. Area 25 must be located forward of the heads of the metatarsal bones, but may be spaced from the anterior plantar foot surface perimeter by a distance greater than d in order to allow the stimulation to be applied rearwardly of the toes.

Figure 2:
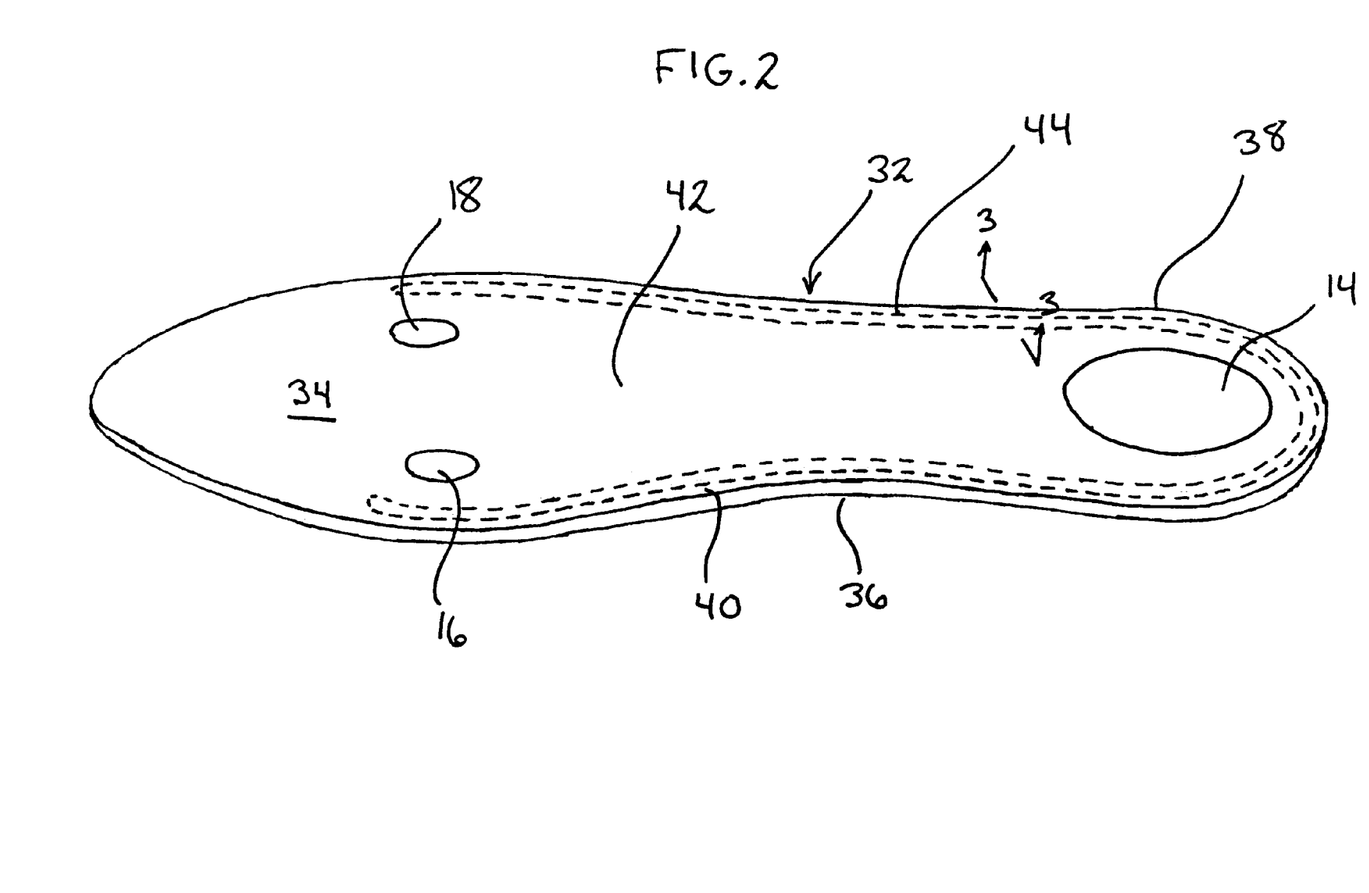
FIG. 2 is a top perspective view of an insole according to a first preferred embodiment of the present invention.

In one preferred embodiment of the present invention, shown in FIG. 2, stimulation of cutaneous sensation is produced by an insole 32 having an upper surface 34, lower surface 36 and outer perimeter 38. For ease of comparison with FIG. 1, FIG. 2 shows the approximate positioning of bones 14, 16 and 18 relative to insole 32. Insole 32 is adapted to be received in a conventional manner on an upper surface of a sole in an article of footwear (not shown), such that its lower surface 36 contacts the upper surface of the sole and its upper surface 34 contacts the plantar foot surface 12 of the wearer of the footwear. Insole 32 comprises an outer peripheral portion 40 and a central portion 42 which is located inwardly of, and surrounded by, the peripheral portion 40.

Central portion 42 of insole 32 preferably comprises a resilient cushioning material, for example a foamed polymeric material. The outer peripheral portion 40 of insole 32 contains at least one ridge-forming member 44 which, in FIGS. 2 and 3, comprises a length of flexible, compliant small diameter tubing or similar structure embedded between upper and lower surfaces 34 and 36. Preferably, the material in which ridge-forming member 44 is embedded in the peripheral portion 40 of insole 32 is the same as that comprising central portion 42, such that the peripheral and central portions 40 and 42 are integrally formed. Ridge-forming member 44 is preferably harder than the surrounding material and has an uncompressed height and width (both of which correspond to outside diameter where the ridge-forming member is a tube) of up to about 8 mm, more preferably not more than about 3 to 6 mm, and most preferably about 3 mm. Although the ridge-forming member 44 shown in FIG. 2 comprises tubing, it is to be appreciated that the narrow ridge-forming member may alternately comprise a series of spaced elements or a narrow, elongate member having any of a variety of cross-sectional shapes and sizes. Most preferably, the narrow, elongate member has a cylindrical or other shape which provides a rounded foot-contacting surface. Furthermore, it is to be appreciated that the ridge-forming member may preferably be integrally formed with the remainder of the insole and may preferably comprise a narrow strip of material having a hardness greater than that of the surrounding material.

As shown in FIG. 2, ridge-forming member 44 extends along, and in close proximity to, the outer perimeter 38 of insole 32. Ridge-forming member 44 is positioned in insole 32 so as to extend continuously along the lateral edge 28 of foot 10 from the head of the fifth metatarsal bone 18 to calcaneus bone 14, around the calcaneus bone 14 and along the medial edge 22 of foot 10 from the calcaneus bone 14 to the head of the first metatarsal bone 16. It will be appreciated that ridge-forming member 44 extends throughout the three areas 20, 26 and 30 shown in FIG. 1 and also through instep 24.

Figure 3:
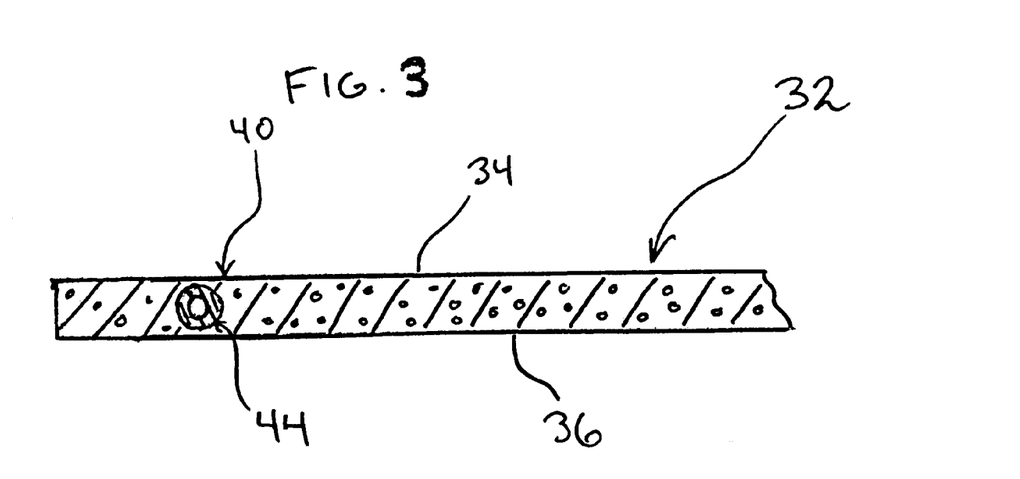
FIG. 3 is a transverse cross-section along the line 3—3 in FIG. 2.
Figure 4:
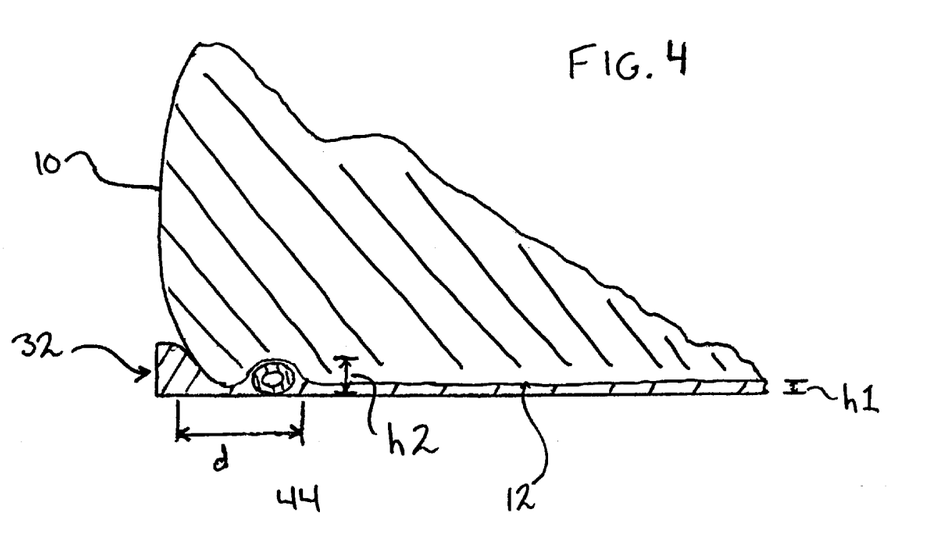
FIG. 4 is a partial transverse cross-section showing the manner in which the insole in FIG. 2 stimulates cutaneous pressure sensation in a human foot.

FIG. 3 shows insole 32 in an uncompressed state with ridge-forming member 44 embedded in peripheral portion 40 of insole 32 such that the upper surface 34 of insole 32 is substantially flat. However, as shown in FIG. 4, when insole 32 is compressed by a human foot 10, for example during standing or walking, the resilient material surrounding ridge-forming member 44 is compressed under the plantar foot surface 12 to a height h1 which is less than a compressed height h2 of ridge-forming member 44. Therefore, when insole 32 is compressed, ridge-forming member 44 forms an elongate, raised ridge which protrudes upwardly against the plantar foot surface 12 of foot 10, the entirety of the raised ridge being within distance d from the perimeter of plantar foot surface 12 and from the perimeter of the insole 32.

As shown in FIG. 4, the protruding raised ridge causes indentation of the plantar foot surface 12. The degree of skin indentation produced by the raised ridge is defined as the difference between height h2 and height h1 in FIG. 4. The degree of skin indentation may be less than the uncompressed height of the ridge-forming member, due to the compression of the ridge-forming member caused by the foot. Preferably, the degree of skin indentation is from about 1 to about 5 mm.

Figure 5:
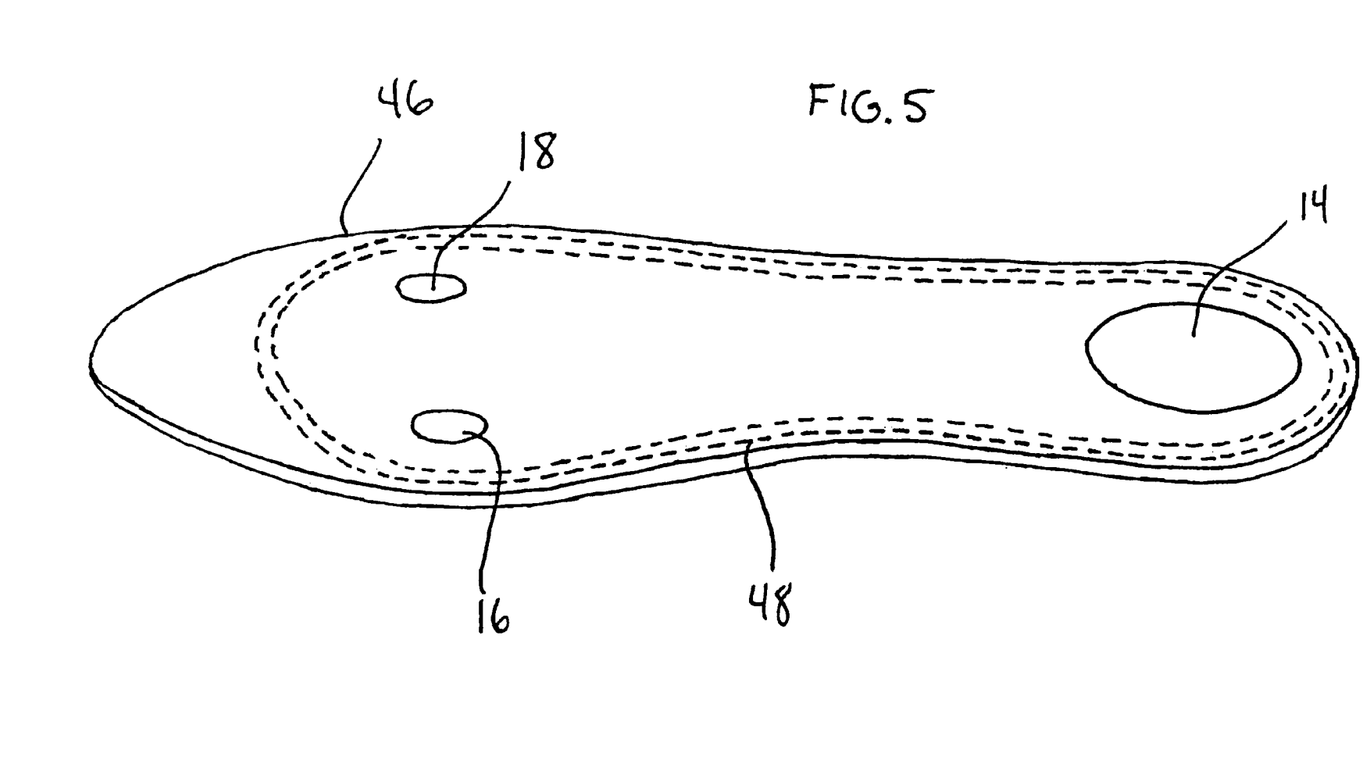
FIG. 5 is a top perspective view of an insole according to a second preferred embodiment of the present invention.

FIG. 5 illustrates a second preferred insole 46 which is identical in all respects to insole 32 except that ridge-forming member 44 of insole 32 is replaced by a ridge-forming member 48. Like member 44 shown in FIG. 2, member 48 extends from the head of the fifth metatarsal bone 18, along the lateral edge 28 of foot 10 to calcaneus bone 14, around calcaneus bone 14, and along the medial edge of foot 10 to the head of the first metatarsal bone 16. However, ridge-forming member 48 also includes a laterally extending portion extending through area 25 shown in FIG. 1.

Figure 6:
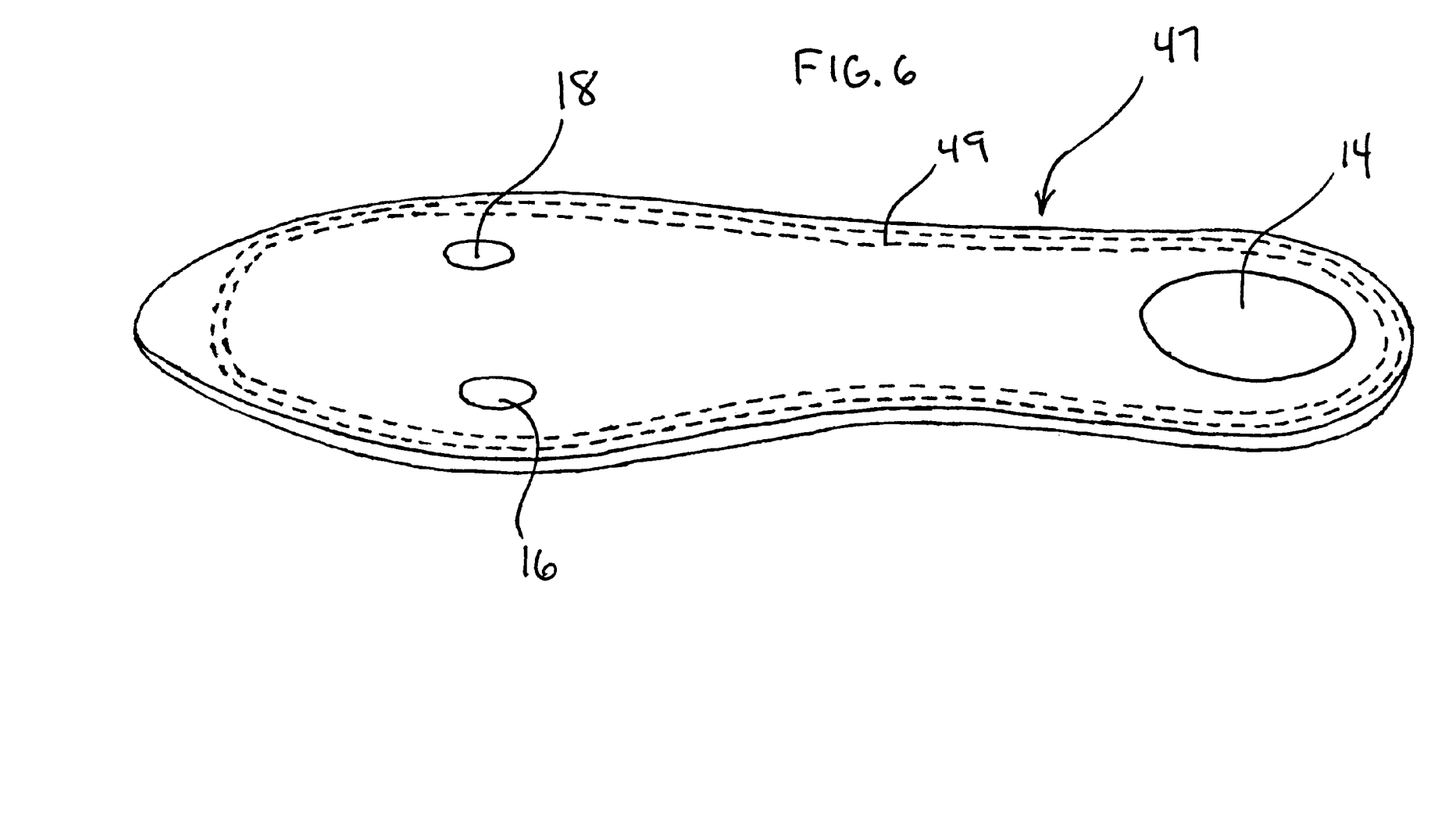
FIG. 6 is a top perspective view of an insole according to a third preferred embodiment of the invention.

FIG. 6 illustrates a third preferred insole 47 which is identical in all respects to insole 32 except that ridge-forming member 44 of insole 32 is replaced by a ridge-forming member 49. Like member 44 shown in FIG. 2, member 49 extends from the head of the fifth metatarsal bone 18, along the lateral edge 28 of foot 10 to calcaneus bone 14, around calcaneus bone 14, and along the medial edge of foot 10 to the head of the first metatarsal bone 16. However, ridge-forming member 49 also includes a laterally extending portion extending through area 27 shown in FIG. 1. This portion of ridge-forming member 49 may be spaced from the periphery of insole 32 by a distance somewhat greater than distance d, so as to pass under one or more of the toes.

Figure 7:
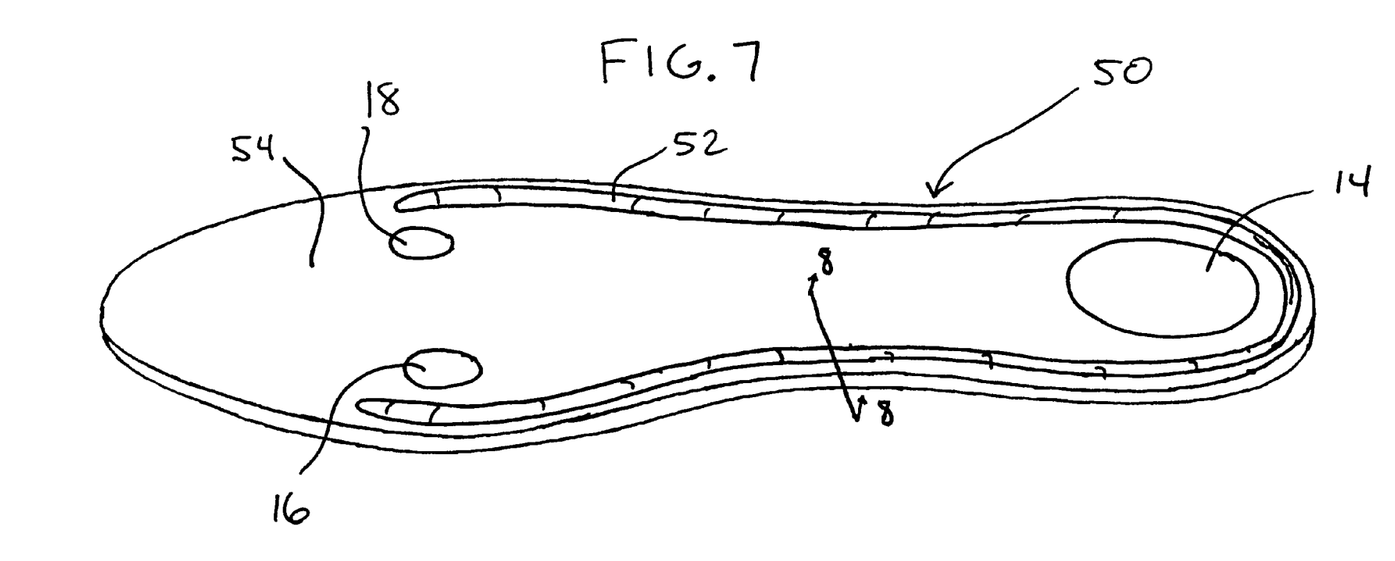
FIG. 7 is a top perspective view of an insole according to a fourth preferred embodiment of the present invention.
Figure 8:
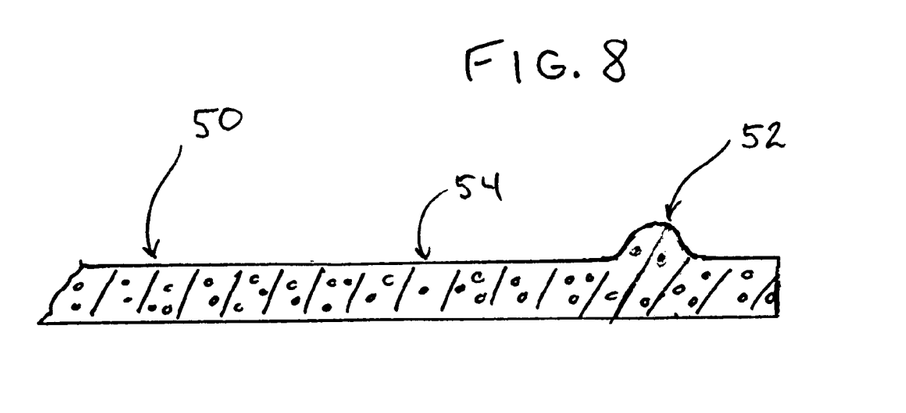
FIG. 8 is a transverse cross-section along the line 8—8 in FIG. 7.

Although insoles 32, 46 and 47 shown in the drawings are substantially flat in an uncompressed state, it is to be appreciated that this is not necessarily the case. For example, FIGS. 7 and 8 illustrate a fourth preferred insole 50 in which the ridge-forming member 52 extends above the upper surface 54 of the insole when the insole 50 is in an uncompressed state. Ridge-forming member 52 comprises an elongate ridge integrally formed with the remainder of insole 50, and preferably formed from the same material as the remainder of insole 50. Preferably, the entire insole 50, including ridge-forming member, is made from a flexible, resilient material such as rubber and foamed polymers. However, it will be appreciated that ridge-forming member 52 may preferably be formed from a material different than that of the material comprising the remainder of insole 50, so long as member 52 forms a raised ridge when the insole 50 is compressed.

Figure 9:
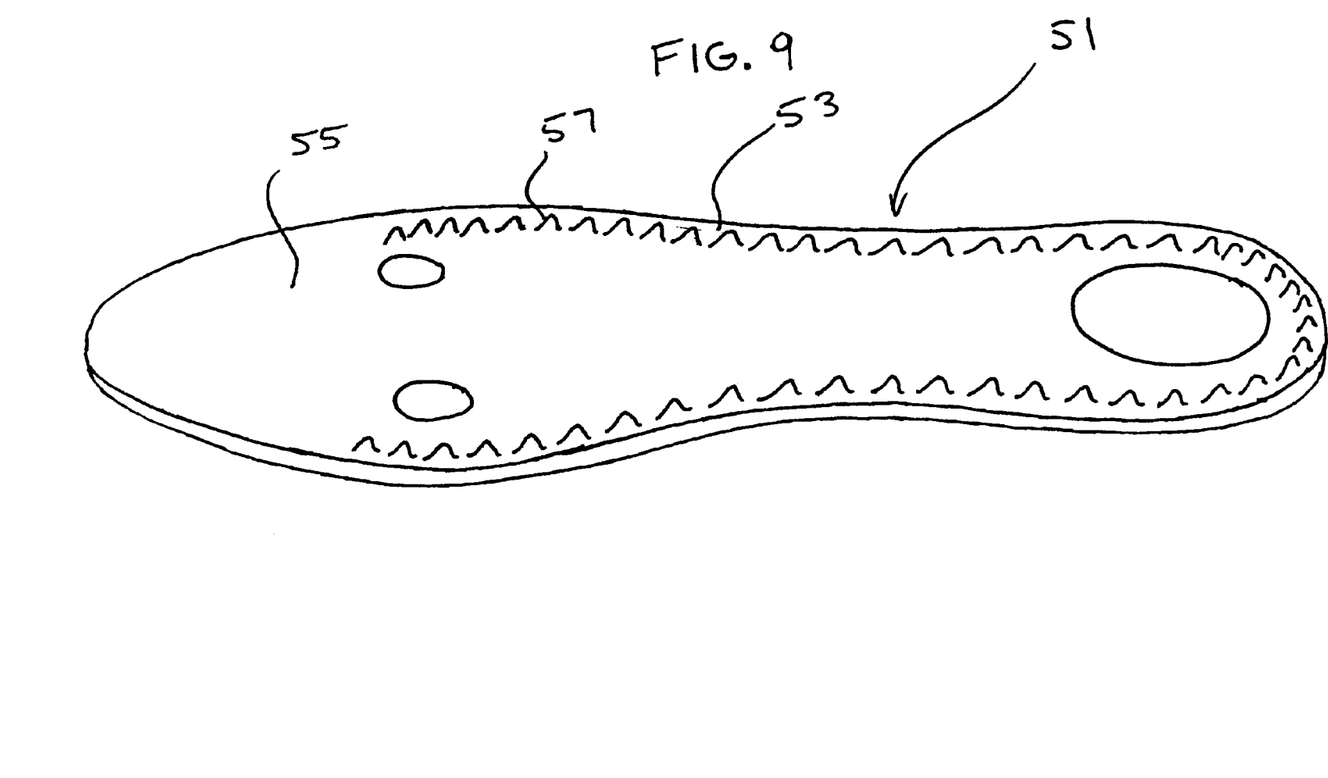
FIG. 9 is a top perspective view of an insole according to a fifth preferred embodiment of the present invention.

FIG. 9 illustrates a fifth preferred insole 51 in which the ridge-forming member 53 extends above the upper surface 55 of the insole when the insole 50 is in an uncompressed state. Ridge-forming member 53 comprises a plurality of spaced, rounded protrusions 57 integrally formed with the remainder of insole 51, and preferably formed from the same material as the remainder of insole 51.

Furthermore, it will be appreciated that the upper surface of the insole is not necessarily planar. For example, the insole may be smoothly contoured to conform to the shape of the bottom of the foot, and may be provided with an arch support or the like, so long as cutaneous stimulation is produced substantially only proximate the perimeter of the plantar foot surface. The insole may be of any desired configuration as long as a raised ridge is formed in close proximity to the perimeter of at least a portion of the plantar foot surface when the adjacent area of the insole is compressed and the areas located inwardly of the raised ridge are smoothly contoured.

Although the preferred embodiments of the invention described above comprise insoles, it is to be appreciated that other preferred configurations of inserts are also within the scope of the invention. For example, an insert may be provided which does not have a central portion inward of the ridge-forming member.

Figure 10:
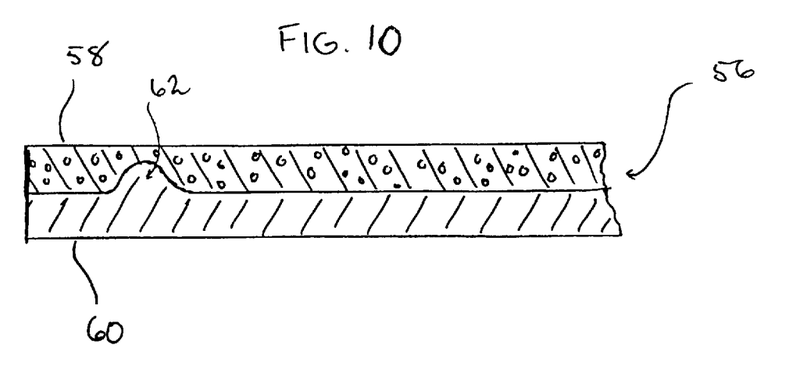
FIG. 10 is a partial transverse cross-section through the sole of an article of footwear according to a preferred embodiment of the invention.
Figure 11:
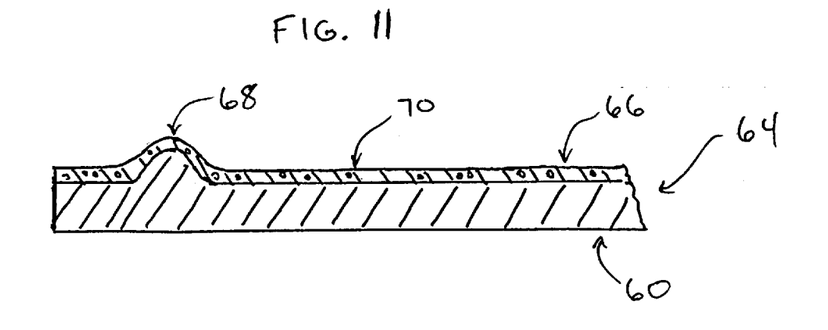
FIG. 11 is a partial transverse cross-section through the sole of an article of footwear according to another preferred embodiment of the invention.
Figure 12:
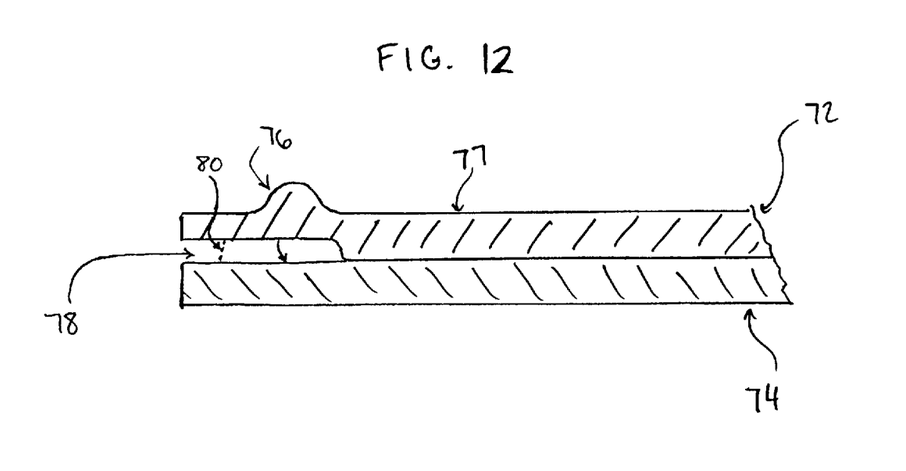
FIG. 12 is a partial transverse cross-section through the sole of an article of footwear according to yet another preferred embodiment of the present invention.

Furthermore, the present invention also includes within its scope articles of footwear comprising an upper and a sole, including but not restricted to shoes, boots, slippers and sandals. FIGS. 10 to 12 comprise partial transverse sectional views through the soles of preferred articles of footwear according to the invention. Other features of the footwear according to the invention are conventional and have been omitted for clarity.

FIG. 10 illustrates two layers of a preferred sole 56 of an article of footwear according to the invention, sole 56 comprising an inner sole 58 and an outer sole 60. Inner sole 58 forms a foot-contacting layer of sole 56 which is preferably formed from a resilient, cushioning material such as a foamed polymeric material. The term "foot-contacting" layer as used herein is intended to indicate that the foot of the wearer is received on an upper surface of the layer. However, it will be appreciated that the foot is not necessarily directly in contact with the foot-contacting layer. Rather, the foot and the foot-contacting layer may be separated by one or more layers of material such as, but not restricted to, hosiery and insoles.

The outer sole 60 shown in FIG. 10 is provided with an integrally molded ridge-forming member 62 having a smoothly rounded upper surface. Ridge-forming member 62 is located adjacent the perimeter of sole 60 so as to stimulate cutaneous sensation from the perimeter of the plantar foot surface, including one or more of areas 20, 25, 26, 27 and 30 shown in FIG. 1. The material from which inner sole 58 is formed is more compressible than the material comprising outer sole 60, so that when sole 56 is compressed during use of the footwear, member 62 forms a raised ridge in close proximity to the perimeter of the plantar foot surface in the manner shown in FIG. 4.

FIG. 11 illustrates two layers of another preferred sole 64 of an article of footwear according to the invention, sole 64 comprising an inner sole 66 and an outer sole 60 identical to that of FIG. 10. In the embodiment of FIG. 11, the inner sole is thinner than in FIG. 10, thereby providing a ridge 68 protruding above the upper surface 70 of inner sole 66.

FIG. 12 illustrates yet another preferred embodiment of the present invention, comprising an insole 72 which is shown as being received on top of a sole 74 of an article of footwear. Insole 72 is received on top of sole 74 and has an integrally formed ridge-forming member 76 protruding from its upper surface 77. Insole 72 and ridge-forming member 76 are preferably substantially identical to insole 50 shown in FIG. 7 with the exception that an air space 78 is formed in an area below the ridge-forming member 76. Air space 78 preferably extends under the entire ridge-forming member 76. The air space 78 increases the compliance of ridge-forming member 76, allowing the portion of insole 72 underlying ridge-forming member 76 to be bent downwardly in the direction of the arrow shown in FIG. 12.

The configuration of air space 78 is variable. In one preferred embodiment, the peripheral edge of insole 72 is undercut to beneath the ridge-forming member 76. In another preferred embodiment, air space 78 is in the form of a channel underlying ridge-forming member 76, with dotted line 80 representing the wall of the channel closest to the periphery of the insole 72.

It will be appreciated that the present invention also includes within its scope an article of footwear having a sole, an inner sole of which comprises insole 72 and an outer sole of which comprises sole 74 of FIG. 12.

The following section describes the findings of a study to determine the efficacy of the present invention in improving postural stability.

EXPERIMENTAL

Studies were conducted involving seven healthy young adults (age 23 to 31) and fourteen healthy older adults (age 65 to 73). Each of the older subjects had a moderate level of cutaneous insensitivity as determined by touch- and vibration-detection tests. Facilitation (stimulation) of cutaneous sensation from the perimeter of the plantar foot surface was provided, in the young-adult study, by a continuous length of flexible polyethylene tubing having an outside diameter of 3 mm, the tubing having a length and orientation as shown in FIG. 2. The tubing used in the older-adult study had a length and orientation as shown in FIG. 5. Perception tests determined that the subjects in both studies were well able to perceive the cutaneous stimulation due to the tubing.

Postural reactions were evoked in each study by horizontal translation of a large (2 m×2 m) moveable platform on which the subject stood. Safety handrails and a harness were used as safety precautions. Sudden transient platform movement (duration 0.6 seconds) in one of four directions (forward, backward, left, right) was used to evoke stepping reactions. Feet-in-place postural reactions, which do not involve stepping, were evoked by means of pseudorandom perturbations in which the platform moved continuously forward and backward or side to side in an unpredictable manner for a period of 96 seconds. Subjects were blindfolded in all trials.

The older adults performed a series of 40 transient-perturbation trials, followed by a series of 16 continuous-perturbation trials. Perturbation direction and magnitude were varied in a random manner. Half of the trials were performed with cutaneous facilitation (i.e. stimulation of sensation by means of the tubing) and the order of testing (with/without facilitation) was balanced across subjects. Subjects were allowed to respond "naturally" in the transient perturbations but were instructed to "try not to step" in the continuous perturbations. A similar protocol was used in the young-adult experiment. The main difference was that a wider range of perturbation magnitudes were used and subjects were instructed to "try not to step" in the transient-perturbation trials. Ground reaction forces were recorded by three forceplates mounted on the platform. Trials were also videotaped for characterization of stepping reactions.

Figure 13:
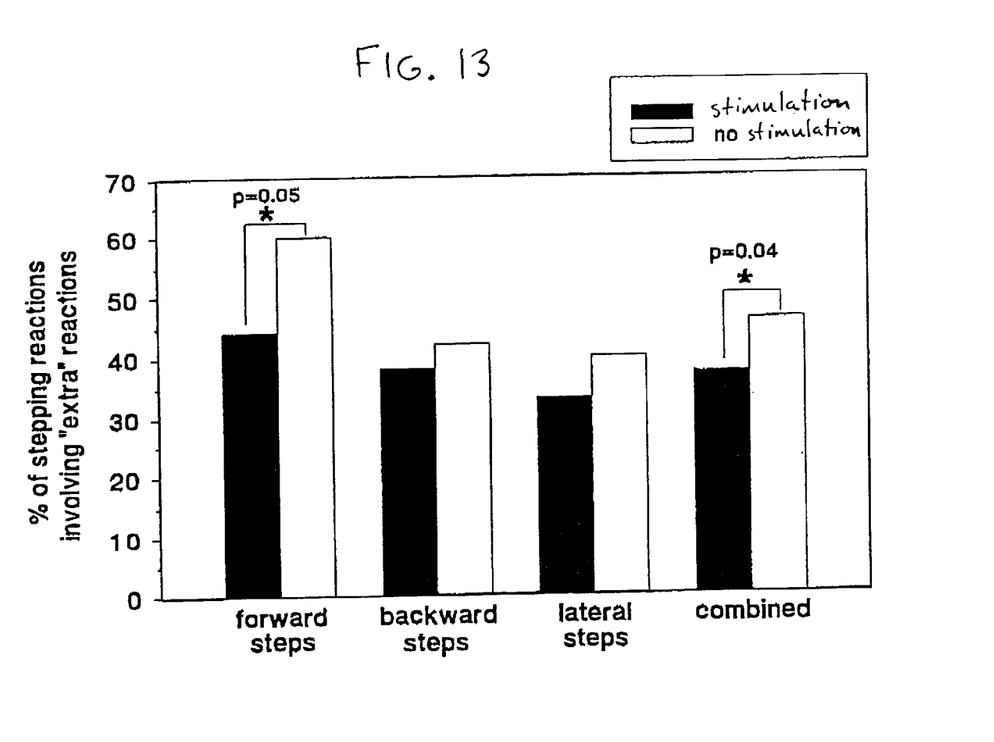
FIG. 13 shows the results of a study in which older adults were exposed to unpredictable, transient (sudden) balance perturbations (disturbances)

The facilitation of cutaneous sensation from the perimeter of the plantar foot surface increased the stability of the stepping reactions that were evoked by sudden platform motion. Without facilitation, 46% of stepping reactions involved multiple reactions (extra steps and/or arm movements), rather than a single stepping reaction. This proportion was reduced to 38% when cutaneous facilitation was provided. The effect of the facilitation was most pronounced for forward steps: 44% of facilitated forward-step reactions involved extra limb movement versus 60% of non-facilitated reactions. In the young-adult study, the facilitation improved the ability to resist stepping in the backward direction by a factor of two: the young adults stepped in 38% of trials when there was no facilitation, but in only 19% of facilitated trials. The results of the transient-perturbation trials in older adults are summarized in FIG. 13, in which the percentage of stepping responses in which "extra" limb reactions (additional steps and/or arm movements) were executed is shown for each direction of stepping: forward, backward and lateral. In addition, the percentage is shown for all directions combined. The percentages were calculated across all fourteen older-adult subjects. Statistically significant differences, due to the cutaneous facilitation, are indicated on the graph (Fisher Exact Test; $p<0.05$).

Figure 14:
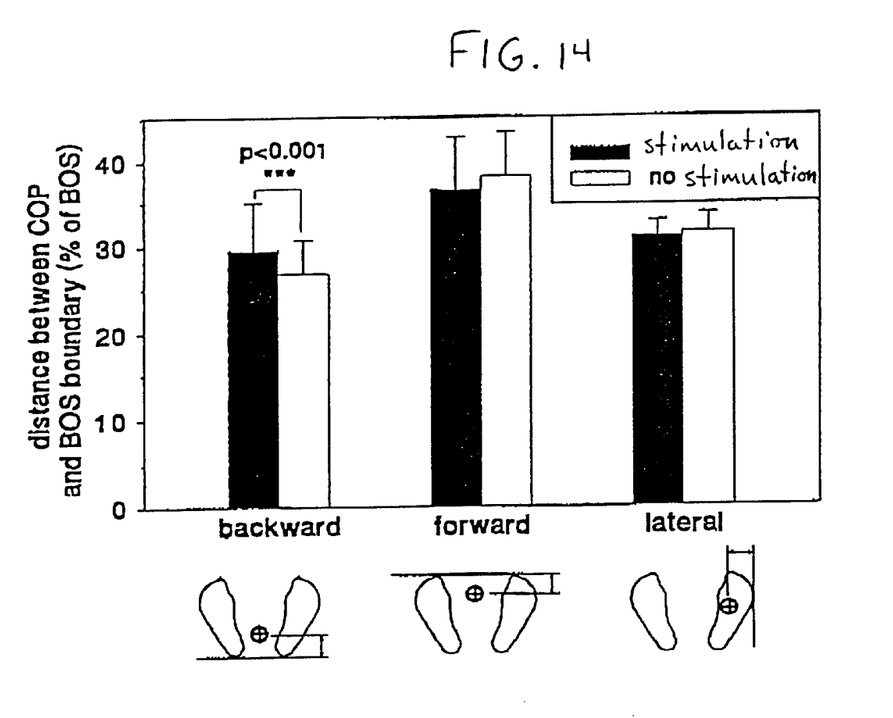
FIG. 14 shows the results of a study in which older adults were exposed to unpredictable and continuous balance perturbations (disturbances).

For the feet-in-place (no stepping) balancing reactions that were evoked by continuous pseudorandom platform motion, the cutaneous facilitation decreased the extent to which the centre of foot pressure (COP) approached the posterior boundary of the base-of-support (BOS) established by the feet. Results of the continuous-perturbation trials in the older adults are illustrated in FIG. 14; similar trends were seen in the young adults. In the figure, the degree to which the COP was allowed to approach the perimeter of the BOS is shown in each of the forward, backward and lateral directions. The forward and backward values were derived from trials involving anterior-posterior perturbation, the lateral values from trials involving medio-lateral perturbation. Each bar represents the mean value, and standard deviation, calculated across all fourteen older adult subjects. The COP values were measured relative to the relevant BOS boundary; hence, smaller values indicate a closer approach to the BOS boundary. To negate variation due to differences in body size, the COP values are expressed as a percentage of the BOS length (for forward and backward COP) or width (for lateral COP). Statistically significant differences, due to the cutaneous facilitation, are indicated in FIG. 14 (Analysis of Covariance; $p<0.05$).

The findings of the above studies provide evidence that facilitation of cutaneous pressure sensation from the plantar foot surface perimeter, due to standing on a narrow raised ridge located in close proximity to the foot surface perimeter, can improve the efficacy of stabilizing postural reactions evoked by unpredictable postural perturbation. Cutaneous stimulation was found to reduce the frequency of multiple reactions (extra steps and/or arm movements) when stepping to recover balance and to limit the extent to which the center of foot pressure approached the posterior foot boundary during feet-in-place reactions. Whereas the effect on stepping likely reflects an improved ability to sense and control foot contact and subsequent weight transfer, the second observation suggests that stimulation of cutaneous sensation from the perimeter of the plantar foot surface may also provide the central nervous system with increased information about the stability limits associated with the base of support established by the feet.

Although the invention has been described in relation to certain preferred embodiments, it is to be understood that the invention is not restricted thereto. Rather, the invention includes all embodiments which may fall within the scope of the following claims.

What is claimed is:

1. A foot-contacting insert for insertion into an article of footwear having a sole, the insert comprising:

upper foot-contacting surface and an opposing, lower sole-contacting surface, the insert having a perimeter substantially conforming in size and shape to a perimeter of a plantar foot surface of a foot of a wearer; and at least one ridge-forming member located in close proximity to the perimeter of the insert such that, when the wearer is standing or walking in the article of footwear in which the insert is received, the at least one ridge-forming member forms a narrow, elongate, raised ridge which protrudes upwardly against the plantar foot surface in a narrow, localized area in close proximity to the perimeter of the plantar foot surface;

wherein the at least one ridge-forming member has an uncompressed height and width of about 3 to 8 mm and is located in its entirety within about 15 mm, or less, of the perimeter of the plantar foot surface; and when the wearer is wearing the article of footwear, the raised ridge extends along the perimeter of the plantar foot surface in at least a portion of a lateral edge of the foot from a fifth metatarsal bone of the foot to a calcaneus bone of the foot; an entire posterior edge of the calcaneus bone; and at least a portion of a medial edge of the foot from the calcaneus bone to a first metatarsal bone of the foot, and all areas of the upper foot-contacting surface of the insert located inwardly of the raised ridge present a smoothly contoured surface to the plantar foot surface.

2. An insert according to claim 1, wherein the insert further comprises a transverse ridge-forming member which forms a narrow, transverse raised ridge extending across a width of the foot and located rearwardly of toes of the foot and forward of the metatarsal bones of the foot.

3. An insert according to claim 1, wherein the insert further comprises a transverse ridge-forming member which forms a narrow, transverse raised ridge extending across a width of the foot and located approximately under a plantar surface of one or more toes.

4. An insert according to claim 1, wherein the narrow ridge-forming member or members comprise a series of spaced protrusions.

5. A foot-contacting insert for insertion into an article of footwear having a sole, the insert comprising:

an upper foot-contacting surface and an opposing, lower sole-contacting surface, the insert having a perimeter substantially conforming in size and shape to a perimeter of a plantar foot surface of a foot of a wearer; and at least one ridge-forming member located in close proximity to the perimeter of the insert such that, when the wearer is standing or walking in the article of footwear in which the insert is received, the at least one ridge-forming member forms a narrow, elongate, raised ridge which protrudes upwardly against the plantar foot surface in a narrow, localized area in close proximity to the perimeter of the plantar foot surface;

wherein the at least one ridge-forming member has an uncompressed height and width of about 3 to 8 mm and is located in its entirety within about 15 mm, or less, of the perimeter of the plantar foot surface;

when the wearer is wearing the article of footwear, the raised ridge extends along the perimeter of the plantar foot surface in at least a portion of a lateral edge of the foot from a fifth metatarsal bone of the foot to a calcaneus bone of the foot; at least a portion of a posterior edge of the calcaneus bone; and at least a portion of a medial edge of the foot from the calcaneus bone to a first metatarsal bone of the foot, and all areas of the upper foot-contacting surface of the insert located inwardly of the raised ridge present a smoothly contoured surface to the plantar foot surface; and wherein the insert comprises an insole having an outer peripheral portion containing the ridge-forming member or members and a central portion comprising a resilient cushioning material such that, when the insole is in an uncompressed state, an upper surface of the outer peripheral portion and an upper surface of the central portion are substantially coplanar.

6. An insert according to claim 1, wherein a bottom surface of the insert is indented to provide an air space under at least one ridge-forming member.

7. An insert according to claim 1, wherein the raised ridge has a height of from about 1 mm to about 5 mm.

8. An article of footwear, including a sole having an upper foot-contacting layer and a perimeter substantially conforming in size and shape to a perimeter of a plantar foot surface of a foot of a wearer of the article of footwear, the sole comprising:

at least one ridge-forming member located in close proximity to the perimeter of the upper foot-contacting layer of the sole such that, when the wearer of the article of footwear is standing or walking in the article of footwear, the at least one ridge-forming member forms a narrow, elongate, raised ridge which protrudes upwardly against the plantar foot surface in a narrow, localized area in close proximity to the perimeter of the plantar foot surface;

wherein the at least one ridge-forming member has an uncompressed height and width of about 3 to 8 mm and is located in its entirety within about 15 mm, or less, of the perimeter of the plantar foot surface; and when the wearer is wearing the article of footwear, the raised ridge extends along the perimeter of the plantar foot surface in at least a portion of a lateral edge of the foot from a fifth metatarsal bone of the foot to a calcaneus bone of the foot; an entire posterior edge of the calcaneus bone; and at least a portion of a medial edge of the foot from the calcaneus bone to a first metatarsal bone of the foot, and all areas of the upper foot-contacting layer of the sole located inwardly of the raised ridge present a smoothly contoured surface to the plantar foot surface.

9. An article of footwear according to claim 8, wherein the upper layer of the sole further comprises a transverse ridge-forming member which forms a narrow, transverse raised ridge extending across a width of the foot and located rearwardly of toes of the foot and forward of the metatarsal bones of the foot.

10. An article of footwear according to claim 8, wherein upper layer of the sole further comprises a transverse ridge-forming member which forms a narrow, transverse raised ridge extending across a width of the foot and located approximately under a plantar surface of one or more toes.

11. An article of footwear according to claim 8, wherein the narrow ridge-forming member or members comprise a series of spaced protrusions.

12. An article of footwear including a sole having an upper foot-containing layer and a perimeter substantially conforming in size and shape to a perimeter of a plantar foot surface of a foot of a wearer of the article of footwear, the sole comprising:

at least one ridge-forming member located in close proximity to the perimeter of the upper foot-contacting layer of the sole such that, when the wearer of the article of footwear is standing or walking in the article of footwear, the at least one ride forming member forms a narrow, elongate, raised ridge which protrudes upwardly against the plantar foot surface in a narrow, localized area in close proximity to the perimeter of the plantar foot surface;

wherein the at least one ridge-forming member has an uncompressed height and width of about 3 to 8 mm and is located in its entirety within about 15 mm, or less, of the perimeter of the plantar foot surface;

when the wearer is wearing the article of footwear, the raised ridge extends along the perimeter of the plantar foot surface in at least a portion of a lateral edge of the foot from a fifth metatarsal bone of the foot to a calcaneus bone of the foot; at least a portion of a posterior edge of the calcaneus bone; and at least a portion of a medial edge of the foot from the calcaneus bone to a first metatarsal bone of the foot, and all areas of the upper foot-contacting layer of the sole located inwardly of the raised ridge present a smoothly contoured surface to the plantar foot surface; and wherein the upper layer of the sole comprises an insole having an outer peripheral portion containing the ridge-forming member or members and a central portion comprising a resilient cushioning material such that, when the insole is in an uncompressed state, an upper surface of the outer peripheral portion and an upper surface of the central portion are substantially coplanar.

13. An article of footwear according to claim 8, wherein a bottom surface of the upper foot-contacting layer of the sole is indented to provide an air space under at least one ridge-forming member.

14. An article of footwear according to claim 8, wherein the raised ridge has a height of from about 1 mm to about 5 mm.

\* \* \* \* \*